United States Patent [19]

Turbe

[11] Patent Number: 4,467,653

[45] Date of Patent: Aug. 28, 1984

[54] METHOD AND APPARATUS FOR ULTRASONIC ANALYSIS

[75] Inventor: Jean-Pierre Turbe, Nanteuil-les-Meaux, France

[73] Assignee: Matix Industries S.A., France

[21] Appl. No.: 362,273

[22] Filed: Mar. 26, 1982

[51] Int. Cl.³ .......................................... G01N 29/00
[52] U.S. Cl. ........................................ 73/620; 73/629
[58] Field of Search ................ 73/620, 618, 627, 629; 128/660; 367/151

[56] References Cited

U.S. PATENT DOCUMENTS

| | | | |
|---|---|---|---|
| 4,084,582 | 4/1978 | Nigam | 73/620 |
| 4,185,501 | 1/1980 | Proudian et al. | 73/641 |
| 4,274,421 | 6/1981 | Dory | 73/620 |
| 4,317,370 | 3/1982 | Glenn | 73/620 |

*Primary Examiner*—Stephen A. Kreitman
*Assistant Examiner*—John E. Chapman, Jr.
*Attorney, Agent, or Firm*—Darby & Darby

[57] ABSTRACT

A transducer located in a reservoir that contains ultrasound-transmitting liquid directs and receives beams of ultrasound onto and from a rotating reflector which is also located in the reservoir. A diaphragm transmits the ultrasound from the liquid to a body which is to be analyzed. The results of the ultrasonic analysis are displayed on a cathode ray tube which is synchronized with the transducer and the rotating reflector.

10 Claims, 1 Drawing Figure

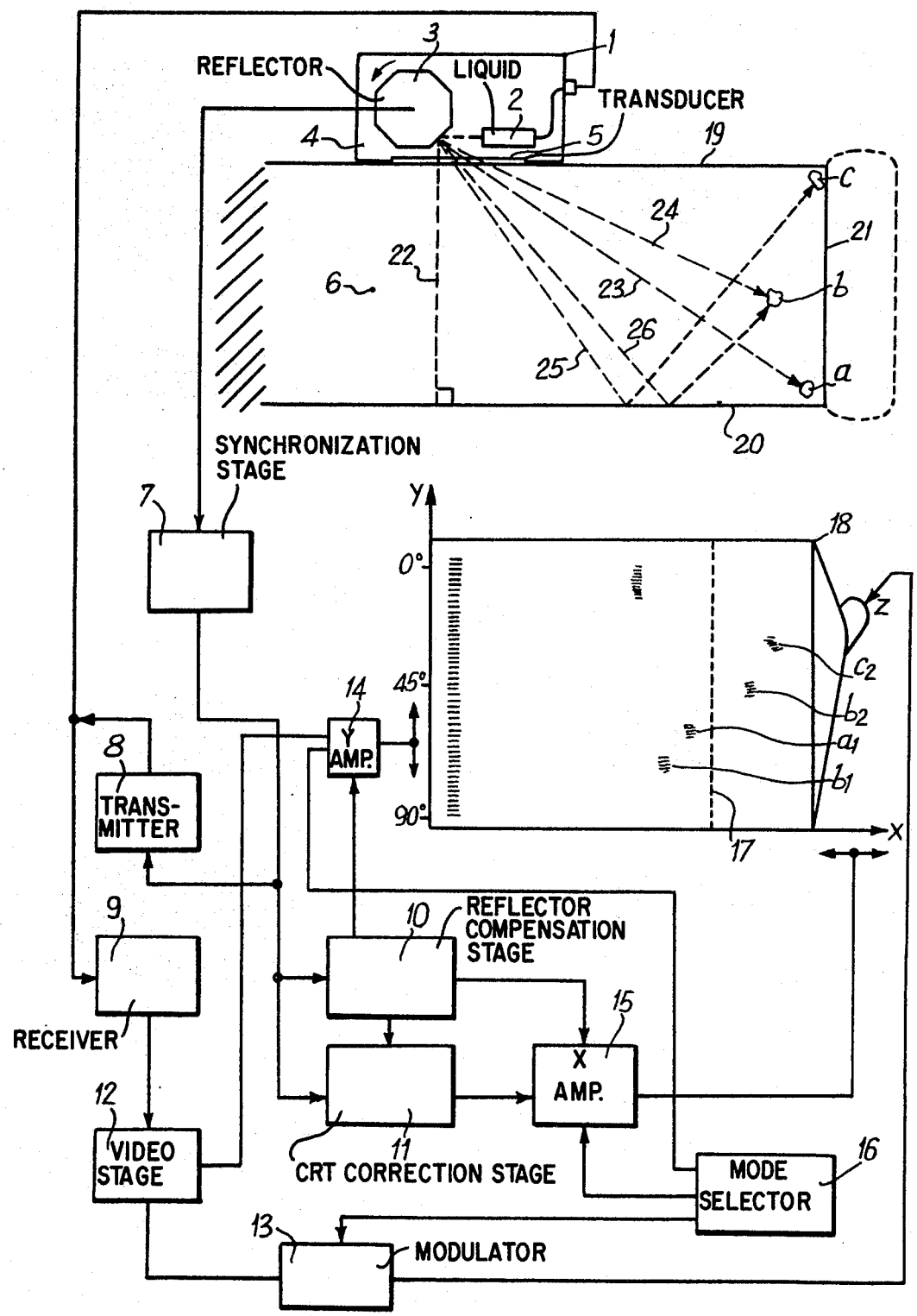

METHOD AND APPARATUS FOR ULTRASONIC ANALYSIS

The present invention relates to a method and apparatus for ultrasonic analysis of a body, and more particularly relates to method and apparatus for ultrasonic analysis with a graphical display of the results of this analysis.

The ultrasonic analysis of a metal part to discover flaws, if any, is known. In this analysis, a source of ultrasound is placed on a body and an observation is made, for example on a graphic paper strip recorder, of the echoes detected along the axis of the source. It is then necessary to move the source step by step over a face of the part to be analyzed, in order to have a graphic representation of its flaws. This movement of the source requires a series of manipulations which extend the period of measurement and make errors more likely.

One object of the invention is to avoid these drawbacks by reducing the measuring time and by eliminating in large measure the movements of the source.

Another object of the invention is to graphically display the results of the ultrasonic analysis by means other than the paper strip of a graphic recorder or plotter.

One aspect of the invention is a process for ultrasonic analysis, in which process a source of ultrasound is placed in the vicinity of a face of the body, the beam of ultrasound transmitted by the source is reflected toward the body by a rotating reflector to insure rotational scanning in one plane of the body, and the graphical image corresponding to the analysis in the plane of the body is displayed on a screen.

Another aspect of the invention is a device for ultrasonic analysis which includes a probe applied to the body, the probe having a source of ultrasound and a rotating reflector; the device having a cathode ray tube for graphic display with two perpendicular axes corresponding respectively to angles and to distances; and the device further having a electronic circuit connecting the probe to the cathode ray tube and insuring synchronous operation of the probe and the cathode ray tube.

According to the invention:

The source of ultrasound and the rotating reflector are immersed in a liquid which transmit the ultrasound.

The probe assembly is ultrasonically linked to the body to be analyzed, by means of an ultrasound transmitting diaphragm.

The cathode ray tube for graphic display provides an image of the flaws observed in the body analyzed, either directly, or indirectly after reflection of the ultrasonic beam on the face of the body opposite the probe.

BRIEF DESCRIPTION OF THE DRAWING

The drawing shows a simplified, schematic block diagram of a preferred embodiment of the invention.

DETAILED DESCRIPTION OF PREFERRED EMBODIMENTS

In the single FIGURE, the probe 1 has a transducer 2 transmitting ultrasonic waves toward a rotating reflector 3, which latter is in the shape of a prism having regular lateral facets. There are six facets in the example shown, but there may be more or less. The assembly of transducer 2 and reflector 3 is immersed in a resevoir containing a liquid 4 that can transmit ultrasound. The probe 1 has a lateral diaphragm 5 that can be applied to one face of the body 6 to be analyzed, and that is capable of transmitting the ultrasound to the body 6. Body 6 has an upper face 19 in contact with diaphragm 5, and a lower face 20 opposite the probe 1. The flaws or inclusions a, b, c are represented (by way of example) adjacent an interface 21 with an adjoining part or a weld, but they may be located elsewhere. Reflector 3 is rotated in the direction of the arrow, and each of its facets acts as a rotating mirror opposite the beam of ultrasounds transmitted by transducer 2. The beam reflected by a facet of the reflector 3 is propagated to diaphragm 5, is refracted, and is then propagated into body 6, in a rectilinear path such as is shown at 22, 23, or 24, for example.

If a flaw (face 20, flaws a or b) is encountered, a part of the beam is reflected off the flaw and returns to the transducer 2 of the probe 1, which transducer serves both for the transmission and the reception of the beam of ultrasound. Although a transducer is used in this example, separate transmitting and receiving units can be used instead.

If the beam meets face 20 at a certain angle (beam 25 or 26, for example) it is reflected by this face and can then strike a flaw such as c or b respectively. The reflection off the flaw then occurs and a part of the beam returns to transducer 2. The detection of these echos then permits the graphic display of the flaws in body 6.

The electronic circuit represented schematically has a transmitter 8 that sends the transducer 2 a signal of adequate frequency for transmission of ultrasound, a receiver 9 for the reception of the echo signals, a video stage 12 that shapes the reception signals for use by a Z-modulator 13 which varies the election beam intensity of cathode ray tube 18. The circuit also has a synchronization stage 7 synchronizing the rotation of reflector 3, (accomplished by outside mechanical means, for example a motor, not shown) and the transmitter 8; a Y amplifier 14 governing the cathode ray tube deflection currents for Y displacement of the electron beam of cathode ray tube 18 from the video signals, and an X amplifier 15 governing the X displacements of the same beam.

The circuit can also (but need not) have a reflector compensation stage 10, for correction or errors caused by the rotation of reflector 3. Since the point of incidence of the ultrasound beam upon a facet of reflector 3 moves entirely across the facet, the path length traversed by the ultrasound between a facet and the transducer 2 will vary as a function of the degree of rotation of the reflector 3. This, in turn, causes the total path length traversed by the ultrasound to change in dependence upon this degree of rotation. This change would, if uncorrected, result in a slightly distorted analysis. Reflector compensation stage 10 corrects for this distortion by adjusting the X and Y displacements of the electron beam in the cathode ray tube 18 in accordance with the output of the synchronization stage 7 and thus in tandem with rotation of the reflector 3.

Additionally, an identical electron beam deflection in cathode ray tube 18 will, if uncorrected, trace out longer lines at the edges of cathode ray tube 18 than at its center, because of the shape of cathode ray tube 18. CRT correction stage 11 corrects for this distortion. CRT correction stage 11 is desirable, but not necessary.

It is also possible (although not necessary) to provide a display mode selector 16 which can change the real time display between A or B modes, discussed below.

The screen of cathode ray tube 18 can be graduated in degrees on the Y axis (Y amplifier 14), and in distance on the X axis (X amplifier 15). The flaws or discontinuities a, b, c are represented by spots on the screen of cathode ray tube 18.

These flaws can be detected directly (i.e. after a direct reflection of the beam of ultrasound) for example $a_1$ and $b_1$, or indirectly (i.e. after reflection of the beam off face 20) for example $b_2$ and $c_2$. Line 17 on the screen of cathode tube 18 symbolizes the limit of direct detection.

The general working of the device will now be described. The mechanical rotation of reflector 3 synchronized by synchronization stage 7 is accompanied by the transmission of ultrasonic signals by transducer 2 under the control of transmitter 8. These signals are sent in sequences which preferably correspond to reflections of the beam of ultrasound off the centers of the facets of the reflector 3.

The synchronization stage synchronizes transmitter 8 and the reflector and CRT compensation stages 10 and 11 respectively. The echo signals received by transducer 2 are sent to receiver 9 and then to video stage 12. After shaping, the video signals are applied to Z modulator 13 and to Y amplifier 14, which also receives the signals from the reflector compensation stage 10. The X amplifier 15, in turn, receives the signals from both the reflector compensation stage 10 and CRT correction stage 11.

The image of the section of body 6 scanned by the beams of ultrasound is displayed on the screen of cathode ray tube 18, either in real time or after storage in a memory (not shown). The image can then be photographed for further study.

The angular displacement can be indicated on the Y scale, which can be graduated in degrees of refraction angle in body 6. The Y amplifier 14 governs the angular measurement scale in synchronization with the displacement of reflector 3 and the reflector compensation stage 10.

The distance of the flaws and the space covered by these flaws are indicated along the X axis on the screen of cathode ray tube 18. The X amplifier 15 receives the signals, corrected and compensated for distance as a function of the types of ultrasonic waves in body 6.

The method and apparatus of the invention is generally applicable to ultrasonic probing of liquid or solid bodies, where the propagation of the ultrasounds may take place normally as a function of the media involved (e.g. the compositions of the liquid 4 and the body 6).

The invention applies in particular to the detection and measurement of discontinuities in a medium, in the search for fissures, inclusions, porosities, coarse-grain structures, or more generally, any form of heterogeneity in a body.

The best known applications are those relating to quality control of solid metallurgical parts of classic steel, stainless steel, aluminum, lead, uranium and any other metal permeable by ultrasonic waves.

The detection of discontinuities at the ends of parts and weld beads, and the search for characteristic metallurgical flaws are facilitated.

The followup of heterogeneity in magnitude and in development of laboratory and test-bench parts is facilitated.

In A-mode display, the magnitude of reflected energy is displayed on the Y-axis, and the X axis displays the distance of a flaw from the pole. Thus, in A-mode display, the importance of a flaw is shown accurately, together with the flaw's distance. Electron beam intensity remains constant. In the B-mode display, the flaw's distance is displayed along the X axis as before, but the angle of the reflector 3 is displayed on the Y axis and the importance of the flaw is reflected in the lightness of the display on the cathode ray tube 18. In the A-mode, the direction of the flaw is not displayed, as it is in the B-mode. B-mode display is shown in the FIGURE.

I claim:

1. Apparatus for the ultrasonic analysis of a body comprising a container provided with a membrane to be applied against the body to be analyzed, said container being filled with an ultra-sound transmitting liquid;
   means for producing a beam of ultrasound energy located in said container;
   reflector means for reflecting said beam of ultrasound energy into the body through said membrane, said reflector means having a multifaceted, prismatic shape, said reflector means being disposed in said container;
   driving means for driving said prismatic reflector in a continuous rotation around its symmetry axis;
   means for displaying two orthogonal axes which correspond to distances and angles to be displayed;
   means for receiving ultrasound energy reflected from said body, and for providing an output signal representative thereof; and
   electronic circuit means for synchronizing said reflector means and said display.

2. The apparatus of claim 1 wherein the means for synchronizing comprises mode selector means for changing a mode in which the graphic display is displayed on the display means.

3. The apparatus of claim 2, wherein the display means comprises a cathode ray tube and the mode selector means changes the graphic display on the cathode ray tube between
   an A-mode in which the second display axis of the graphic display corresponds to an intensity of an ultrasonic echo and in which electron beam intensity is constant, and
   a B-mode in which the second display axis of the graphic display corresponds to a degree of rotation of the reflector means and in which electron beam intensity is varied with said intensity of an ultrasonic echo.

4. The apparatus of claim 1, wherein the means for synchronizing further comprises means for compensating the graphic display for distortion arising from rotation of the reflector means.

5. The apparatus of claim 1, wherein the ultrasonic transducer is connected to a transmitter and a receiver and the transmitter and receiver are synchronized with the rotation of the reflector means.

6. The apparatus according to claim 1 wherein said display means comprises a cathode ray tube.

7. Apparatus as claimed in claim 1 in which the driving means drives the reflector means in continuous rotation at a constant speed.

8. Apparatus as claimed in claim 7 in which the electronic control circuit comprises a transmitter and a receiver coupled to an ultrasonic transducer, both transmitter and receiver being synchronized with the rotation of the reflector means.

9. Apparatus according to claim 1 wherein said driving means is disposed in said container.

10. Apparatus for ultrasonic analysis of a body comprising:

transducer means for producing and receiving a beam of ultrasound energy;

means for scanning said body along a single direction with said beam of ultrasound energy, said scanning means including reflector means having a plurality of reflecting surfaces for reflecting said ultrasound energy beam along said single direction, said reflector means rotating about an axis of symmetry parallel to said surfaces of said reflector;

means for receiving ultrasound energy reflected from said body;

display means having first and second perpendicular display axis for displaying a graphic display corresponding to said reflected energy; and means for synchronizing said reflector means and said display means so that said first display axis of said graphic display corresponds to a distance between a flaw in said body and said reflector means.

* * * * *